(12) United States Patent
Harbindu

(10) Patent No.: US 11,814,734 B2
(45) Date of Patent: Nov. 14, 2023

(54) 1,2,4-TRIAZOLO[1,5-A] PYRIMIDINE DERIVATIVE AS COPPER CORROSION INHIBITOR

(71) Applicant: ECOLAB USA INC., St. Paul, MN (US)

(72) Inventor: Anand Harbindu, Pune (IN)

(73) Assignee: ECOLAB USA INC., St. Paul, MN (US)

( * ) Notice: Subject to any disclaimer, the term of this patent is extended or adjusted under 35 U.S.C. 154(b) by 423 days.

(21) Appl. No.: 16/868,752

(22) Filed: May 7, 2020

(65) Prior Publication Data
US 2020/0362467 A1 Nov. 19, 2020

Related U.S. Application Data

(60) Provisional application No. 62/847,009, filed on May 13, 2019.

(51) Int. Cl.
*C23F 11/14* (2006.01)
*C07D 487/04* (2006.01)
(Continued)

(52) U.S. Cl.
CPC .............. *C23F 11/149* (2013.01); *C02F 5/12* (2013.01); *C07D 487/04* (2013.01); *C02F 1/72* (2013.01);
(Continued)

(58) Field of Classification Search
CPC ........... C23F 11/00; C23F 11/04; C23F 11/06; C23F 11/08; C23F 11/10; C23F 11/12;
(Continued)

(56) References Cited

U.S. PATENT DOCUMENTS 2,443,136 A 6/1948 Heimback
2,837,521 A 6/1958 Burness
(Continued)

FOREIGN PATENT DOCUMENTS

CN 101824621 9/2010
CN 101824621 A * 9/2010
(Continued)

OTHER PUBLICATIONS

Lahmidi et al. ("Corrosion inhibition of mild steel by two new 1,2,4-triazolo[1,5-a] pyrimidine derivatives in 1 M HCl: experimental and computational study." JMES, 2017, 8(1), pp. 225-237) (Year: 2017).*

(Continued)

*Primary Examiner* — Matthew R Diaz
(74) *Attorney, Agent, or Firm* — Eric D. Babych; Barnes & Thornburg LLP

(57) ABSTRACT

The present disclosure relates to corrosion inhibitor compositions, formulations, and compounds. The compositions, formulations, and compounds may be used is various methods to inhibit corrosion of metallic surfaces in aqueous environments. The corrosion inhibitor compositions may include one of the following compounds or any combination of any of the compounds of formula (I):

18 Claims, 1 Drawing Sheet

(51) Int. Cl.
- *C02F 5/12* (2023.01)
- *C02F 1/72* (2023.01)

(52) U.S. Cl.
- CPC ...... *C02F 2303/08* (2013.01); *C02F 2303/22* (2013.01)

(58) Field of Classification Search
- CPC ....... C23F 11/128; C23F 11/14; C23F 11/146; C23F 11/148; C23F 11/149; C02F 5/10; C02F 5/12; C02F 2303/08; C02F 2303/22
- See application file for complete search history.

(56) References Cited

U.S. PATENT DOCUMENTS

| | | | |
|---|---|---|---|
| 3,939,084 A * | 2/1976 | Sullivan | C09K 3/00 252/77 |
| 4,988,812 A | 1/1991 | Kim et al. | |
| 5,231,094 A | 7/1993 | Bru-Magniez et al. | |
| 5,424,007 A * | 6/1995 | Pera | A01N 43/90 422/18 |
| 5,753,665 A | 5/1998 | Sargent et al. | |
| 5,994,360 A | 11/1999 | Pfrengle | |
| 6,234,811 B1 | 5/2001 | Balkenhohl et al. | |
| 7,026,478 B2 | 4/2006 | Furstner et al. | |
| 7,316,603 B2 * | 1/2008 | Carter | C23F 3/06 451/36 |
| 7,367,870 B2 * | 5/2008 | Kurata | C23F 3/06 451/36 |
| 8,084,362 B2 * | 12/2011 | Amanokura | C23F 3/04 438/692 |
| 8,609,541 B2 * | 12/2013 | Tanaka | C23F 3/04 438/692 |
| 8,741,390 B2 | 6/2014 | Abys et al. | |
| 8,771,665 B2 | 7/2014 | Lee et al. | |
| 9,299,573 B2 * | 3/2016 | Mishima | C23F 3/06 |
| 9,707,215 B2 | 7/2017 | Lee et al. | |
| 10,669,637 B2 * | 6/2020 | Harbindu | C23F 11/149 |
| 2005/0181609 A1 | 8/2005 | Kurata et al. | |
| 2008/0261025 A1 | 10/2008 | Abys et al. | |
| 2008/0314283 A1 | 12/2008 | Abys et al. | |
| 2009/0121192 A1 | 5/2009 | Abys et al. | |
| 2010/0291303 A1 | 11/2010 | Abys et al. | |
| 2010/0319572 A1 * | 12/2010 | Abys | C23C 22/03 106/14.42 |
| 2013/0116236 A1 | 5/2013 | Adam et al. | |
| 2014/0142122 A1 | 5/2014 | Punnonen et al. | |
| 2014/0288046 A1 | 9/2014 | Adam et al. | |
| 2016/0176882 A1 | 6/2016 | Chan et al. | |
| 2016/0177170 A1 * | 6/2016 | Janak | C23F 11/04 507/242 |
| 2016/0211053 A1 | 7/2016 | Hase et al. | |
| 2016/0264533 A1 | 9/2016 | Nomura et al. | |
| 2016/0348253 A1 | 12/2016 | Harbindu et al. | |
| 2018/0043497 A1 | 2/2018 | Hanano et al. | |
| 2019/0352537 A1 * | 11/2019 | Ono | C09G 1/00 |

FOREIGN PATENT DOCUMENTS

| | | |
|---|---|---|
| CN | 102653539 A | 9/2012 |
| CN | 106478639 B | 9/2018 |
| DE | 2533120 A1 | 2/1977 |
| DE | 246999 A1 | 6/1987 |
| DE | 276284 A1 | 2/1990 |
| EP | 1505639 A1 | 2/2005 |
| EP | 2703062 A1 | 3/2014 |
| FR | 2574432 A1 | 6/1986 |
| FR | 2765875 A1 | 1/1999 |
| HU | 205762 B | 6/1992 |
| JP | 48031894 B1 | 10/1973 |
| JP | 48034220 B1 | 10/1973 |
| JP | 48035456 B1 | 10/1973 |
| JP | S56127383 A | 10/1981 |
| JP | S57175193 A | 10/1982 |
| JP | S62273980 A | 11/1987 |
| JP | H0765352 | 3/1995 |
| JP | H10114774 A | 5/1998 |
| JP | 2002134442 | 5/2002 |
| JP | 2015078411 A | 4/2015 |
| JP | 2015079647 | 4/2015 |
| PL | 188652 B1 | 3/2005 |
| PL | 414762 A1 | 5/2017 |
| PL | 231234 B1 | 2/2019 |
| WO | 1998037081 A1 | 8/1998 |
| WO | 1999041255 A1 | 8/1999 |
| WO | 2000056292 A2 | 9/2000 |
| WO | 2000056336 A2 | 9/2000 |
| WO | 2000056733 A1 | 9/2000 |
| WO | 2003094216 A1 | 11/2003 |
| WO | 2004011467 A1 | 2/2004 |
| WO | 2005032256 A1 | 4/2005 |
| WO | 2007012598 A1 | 2/2007 |
| WO | 2007099092 A1 | 9/2007 |
| WO | 2007116011 A2 | 10/2007 |
| WO | 2007120259 A2 | 10/2007 |
| WO | 2009047514 A1 | 4/2009 |
| WO | 2009067446 A1 | 5/2009 |
| WO | 2009082691 A1 | 7/2009 |
| WO | 2010018868 A1 | 2/2010 |
| WO | 2010030224 A1 | 3/2010 |
| WO | 2010112484 A1 | 10/2010 |
| WO | 2010112485 A1 | 10/2010 |
| WO | 2014119752 A1 | 8/2014 |
| WO | 2015164508 A1 | 10/2015 |
| WO | 2016018773 A1 | 2/2016 |
| WO | 2016040417 A1 | 3/2016 |
| WO | 2016073424 A1 | 5/2016 |
| WO | 2016134042 A2 | 8/2016 |
| WO | 2017035528 A1 | 3/2017 |
| WO | 2017056979 | 4/2017 |

OTHER PUBLICATIONS

Saad et al. ("Corrosion inhibition of mild steel in acidic solutions using 1,2,4-triazolo[1,5-a] pyrimidine," Russian Journal of Applied Chemistry, vol. 91, No. 2, 2018, pp. 245-252) (Year: 2018).*

Fettouhi et al. ("7-Ethoxycarbonylmethyl-5-methyl-1,2,4-triazolo[1,5-a]pyrimidine" Acta Cryst., 1996, C52, 1031, abstract only) (Year: 1996).*

Rasheeda et al. ("Pyrimidine derivatives as potential corrosion inhibitors for steel in acid medium," Int. J. Corros. Scale Inhib., 2018, 7, No. 1, 48-61) (Year: 2018).*

Fischer ("Recent advances in 1,2,4-triazolo[1,5-a]pyrimidine chemistry," Advances in Heterocyclic Chemistry, vol. 128, 2019) (Year: 2019).*

Fischer. G., Recent Progress in 1,2,4-Triazolo[1,5-a]pyrimidine Chemistry, Advances in Heterocyclic Chemistry (Jan. 1, 2007) 95, 143-219.

Lahmidi, S., et al., Corrosion inhibition of mild steel by two new 1,2,4-triazolo [1,5-a] pyrimidine derivatives in 1 M HCl: Experimental and computational study, Journal of Materials and Environmental Sciences (2017) 8(1), 225-237.

Saad, I.R., et al., Corrosion Inhibition of Mild Steel in Acidic Solutions Using 1,2,4-Triazolo[1,5-a]pyrimidine, Russian Journal of Applied Chemistry (2018) 91(2), 245-252.

Kuenstlinger, M. et al. "Triazolo[1,5-a]- and -[4,3-a]pyrimidine from 3-alkoxyacrolein and 3-amino-1,2,4-triazoles," Synthesis (1983), (1), pp. 44-47, with English abstract.

Allen, C.F.H. et al. "The Structure of Certain Polyazaindenes. I. Absorption Spectra." Journal of Organic Chemistry (1959), 24, 779-787.

Allen, C.F.H. et al. "The Structure of Certain Polyazaindenes. IV. Compounds from Beta-Keto Acetals and Beta-Methoxyvinyl Ketones." Journal of Organic Chemistry (1959), 24, 796-801.

Bajwa, Joginder S. et al. "Synthesis and structure of some azolo[alpha]pyrimidines, 2,6, 7,8-dTetrahydro-1H-cyclopenta [e]azolo[alpha]pyrimidines, 7,8-Dihydro-6H-cyclopental[f]-s-triazolo[4,3-beta]pyridazine, 5,6,7,8-Tetrahydro-azolo[beta] quinazolines, 6,7,8,9-Tetrahydro-azolo[alpha]quinazolines, and 7,8,9,10-

(56) References Cited

OTHER PUBLICATIONS

Tetrahydro-s-triazolo[3,4-alpha]phthalazine." Journal of the Chemical Society, Perkin Transactions 1: Organic and Bio-Organic Chemistry (1972-1999) (1979), (12), 3085-3094.

Balkaran, Jeral M. et al. "Coordination chemistry of substituted [1,2,4]triazolo[1,5-alpha]pyrimidines with first-row transition-metal ions: Synthesis, spectroscopy and single-crystal structure analysis." Inorganica Chimica Acta (2009), 362(3), 861-868.

Bavelaar, Koen et al. "A dinuclear silver compound with 5,6,7-trimethyl-[1,2,4]triazolo[1,5-alpha]pyrimidine with a short Ag—Ag bond. Synthesis, characterization, single-crystal structure analysis and cytostatic activity." Inorganica Chimica Acta (2011), 366(1), 81-84.

Bee, J.A. et al. "s-Triazolopyrimidines. IV. Synthesis as Potential Therapeutic Agents." Journal of the Chemical Society [Section] C: Organic (1966), (22), 2031-2038.

Brown, Desmond J. et al. "Isomerizations Akin to the Dimroth Rearrangement. III. The Conversion of Simple s-Triazolo [4,3-alpha]pyrimidines into their [1,5-alpha] Isomers." Australian Journal of Chemistry (1977), 30(11), 2515-2525.

Cornelissen, J.P. et al. "Structures and Properties of Bis(Thiocyanato-N)Bis(6-Methyl[1,2,4]Triazolo[1,5-alpha] Pyrimidine-N3)Copper(II), A Distorted Tetrahedral Copper(II) Thiocyanate Compound, and Bis(Thiocyanato-N)Bis(5-Methyl[1,2,4]Triazolo[1,5-alpha]Pyrimidine-N3)Copper(II), A Polynuclear Pseudo-layered System." Polyhedron (1989), 8(18), 2313-2320.

Egner, Ursula et al. "Design of Inhibitors of Photosystem II Using a Model of the D1 Protein." Pesticide Science (1996), 47(2), 145-158.

Elotmani, Bouchaib et al. "Synthesis of New 7(5)-[benzimidazol-2-yl]methyl-5(7)-methyl-1,2,4-triazolo[1,5-alpha](4,3-alpha)pyrimidinies." Comptes Rendus Chimie (2002), 5(6-7), 517-523. (Journal article not available; English abstract only).

Etman, Hassan A. "Enamine rearrangement of pyrimidinium salts. Part XI: Novel synthesis of some pyrazolo and triazolopyrimidine derivatives." Alexandria Journal of Pharmaceutical Sciences (1994), 8(2), 150-153. (Journal article not available; English abstract only).

Fandzloch, Marzena et al. "In search of new anticancer drug—Dimethylsulfoxide ruthenium(III) complex with bulky triazolopyrimidine derivative and preliminary studies towards understanding the mode of action." Polyhedron (2018), 141, 239-246.

Furstner, Alois et al. "Iron-Catalyzed Cross-Coupling Reactions." Journal of the American Chemical Society (2002), 124(46), 13856-13863.

Grodzicki, A. et al. "The molecular structures of copper(II) chloroacetate complexes with 5,7-dimethyl-1,2,4-triazolo-[1,5-alpha]-pyrimidine and 5,7-diphenyl-1,2,4-triazolo-[1,5-alpha]-pyrimidine." Polyhedron (1999), 18(3-4), 519-527.

El Hafi, Mohamed et al. "Ethyl 2-allyl-2-(5-methyl-1,2,4-triazolo[1,5-alpha]pyrimidin-7-yl)pent-4-enoate." IUCrData (2017) 2, 1-8.

Hoffmann, Kamil et al. "Rational design of dicarboxylato platinum(II) complexes with purine-mimetic ligands as novel anticancer agents." Journal of Inorganic Biochemistry (2017), 172, 34-45.

Hori, Mikio et al. "An Unexpected Double Cycloaddition of [1,2,4]Triazolo[1,5-alpha]pyrimidine N-ylide with Activated Acetylenes and Alkenes." Journal of the Chemical Society, Perkin Transactions 1: Organic and Bio-Organic Chemistry (1972-1999) (1987), (1), 2531-2537.

Jakubowski, Mateusz et al. "Dicarboxylato platinum(II) complexes containing dimethyl sulfoxide and triazolopyrimidine as potential anticancer agents: synthesis, structural and biological studies in solution." New Journal of Chemistry (2018), 42(10), 8113-8122.

Khadem, EI et al. "Synthesis and rearrangements of imidazolo- and triazolodiazines." Heterocycles (1989), 28(1), 239-248. (Journal article not available; English abstract only).

Kolosov, Maksim A. et al. "A synthesis of 6-functionalized 4,7-dihydro[1,2,4]triazolo[1,5-alpha]pyrimidines." Tetrahedron Letters (2017), 58(12), 1207-1210.

Kost, A.N. et al. "Isomerization of 5,7-dimethyltriazolo[4,3-alpha]pyrimidine in the presence of alkaline agents." Khimiya Geterotsiklicheskikh Soedinenii (1976), (5), 706-708. (Russian journal article not available; English abstract only).

Williams, L.A. "The Structure of Certain Polyazaindenes. Part VI. The Structure of Some Products Obtained from 3-Amino-1,2,4-triazoles with Acetylacetone and Ethyl Acetoacetate." Journal of the Chemical Society (1960) 1829-1832.

Lahmidi, S. et al. "Corrosion inhibition of mild steel by two new 1,2,4-triazolo[1,5-alpha] pyrimidine derivatives in 1 M HCl: Experimental and computational study." Journal of Materials and Environmental Sciences (2017), 1, 225-237.

Li, Yupeng et. al. "Design, Synthesis, and Biological Evaluation of 3-(1H-1,2,3-Triazol-1-yl)benzamide Derivatives as Potent Pan Bcr-Abl Inhibitors Including the Threonine315-Isoleucine315 Mutant." Journal of Medicinal Chemistry (2012), 55(22), 10033-10046.

Makisumi, Yasuo. "Synthesis of Potential Anticancer Agents. IX. Condensation of some 2-, 5-, and 7-methyl-s-triazolo [2,3-alpha]-pyrimidines with Benzaldehyde." Chemical & Pharmaceutical Bulletin (1961), 9, 883-889.

Okae, Takayuki, et al. "Dialkyl Bicyclic Heterocycles with a Bridgehead Nitrogen as Purine Analogs Possessing Significant Cardiac Inotropic Activity." Journal of Heterocyclic Chemistry (1983), 20(3), 735-751.

Paudler, William W. et al. "Position of Protonation and of N-Methylation in the s-Triazolo[1,5-alpha]pyrimidine Ring System." Journal of Heterocyclic Chemistry (1968), 5(5), 691-693.

Paudler, William W. et al. "Ten Pi-Eectron Nitrogen Heterocyclic Compounds: X The Syntheses and Structure Determinations of Some 1,2,4-triazolopyrimidines." Journal of Heterocyclic Chemistry (1966), 3(3), 269-271.

Polanc, S. et al. "Heterocycles. CXVIII. A Novel Method of Annelation of the 1,2,4-Triazole Ring of the N2—C3 Bond to Azines." Journal of Organic Chemistry (1974), 39(15), 2143-2147.

Polanc, S. et al. "A Novel Synthesis of s-Triazoloazines Fused at the Nitrogen-2-Carbon-3 Bond of the Triazole Ring." Tetrahedron Letters (1973), (19), 1677-1680.

Sirakawa, Kenzo. "Studies on Pyrimidine Derivatives. V. [1,2,4]Triazolopyrimidines (4) ." Yakugaku Zasshi (1959), 79, 1482-1487. (with English abstract).

Sirakawa, Kenzo. "Studies on Pyrimidine Derivatives. III. [1,2,4]Triazolopyrimidines (3) ." Yakugaku Zasshi (1959), 79, 903-907. (with English abstract).

Sirakawa, Kenzo. "Studies on Pyrimidine Derivatives. IX. Mercapto-s-triazolopyrimidines." Yakugaku Zasshi (1960), 80, 1542-1550. (with English abstract).

Spickett, R.G.W. et al. "Bicyclic Pyrimidine Derivatives with a Bridgehead Nitrogen Atom. Part I. Synthesis of s-Triazolo [4,3-alpha]pyrimidines." Journal of the Chemical Society [Section] C: Organic (1967), (6), 498-502.

Stanovnik, Branko et al. "An Unequivocal Synthesis of Some Substituted 1,2,4-triazolo[1,5-alpha]Pyrimidines." Monatshefte fuer Chemie (1987), 118(5), 601-606. (with English abstract).

Stanovnik, Branko et al. "Reactions of N-Heteroarylformamide Oximes and N-Heteroarylacetamide Oximes with N,N-Dimethylformamide Dimethyl Acetal. Synthesis of 2-Methyl-s-triazolo[1,5-x]azines and N-Methylcyanoaminoazines." Journal of Heterocyclic Chemistry (1982), 19(3), 577-583.

Tamura, Yasumitsu et al. "A General Synthesis of s-Triazolo[1,5-x]diazines (1)." Journal of Heterocyclic Chemistry (1975), 12(1), 107-110.

Vartanyan, M.M. et al. "Reaction of 1,1-diacetylcyclopropane with 3-amino-1,2,4-triazole as a new method for the synthesis of 6-functionally substituted 1,2,4-triazolo[1,5-alpha]pyrimidines." Russian Chemical Bulletin (1993), 42(7), 1265-1266.

Al-Shiekh, Mariam A. et al. "alpha-Enones in heterocyclic synthesis, Part I. Classical synthetic and environmentally friendly synthetic approaches to alkyl and acyl azoles and azines," Journal of Chemical Research (2004), 3, 174-179.

Elotmani, Bouchaib et al. "Synthesis of new 7(5)-[benzimidazol-2-yl]methyl-5(7)-methyl-1,2,4-triazolo[1,5-a]([4,3-a]) pyrimidines," Comptes Rendus Chimie (2002), 5(6-7), 517-523 (with English abstract).

(56) References Cited

OTHER PUBLICATIONS

Gamal-Eldeen, Amira M. et al. "Induction of intrinsic apoptosis pathway in colon cancer HCT-116 cells by novel 2-substituted-5,6,7,8-tetrahydronaphthalene derivatives," European Journal of Medicinal Chemistry (2014), 77, 323-333.

Gunay, Esref et al. "Red and Blue Compounds Formed from Copper(II) Bromide and the Ligand 7-Isobutyl-5-methyl-[1,2,4]triazolo[1,5-alpha]pyrimidine: Synthesis, Spectroscopy and Single-Crystal Structures," Journal of Chemical Crystallography (2010), 40(11), 1006-1010.

Ikizler, Aykut A. et al. "Synthesis and Antibacterial Activities of Some 1,2,4-Triazole Derivatives," Acta Poloniae Pharmaceutica (1999), 56(4), 283-288.

Reichardt, Christian et al. "Syntheses with aliphatic dialdehydes. XXXV. Syntheses with 1- and 2-adamantylmalonaldehyde," Zeitschrift fuer Naturforschung, Teil B: Anorganische Chemie, Organische Chemie (1982), 37B(9), 1187-1195 (with English abstract).

* cited by examiner

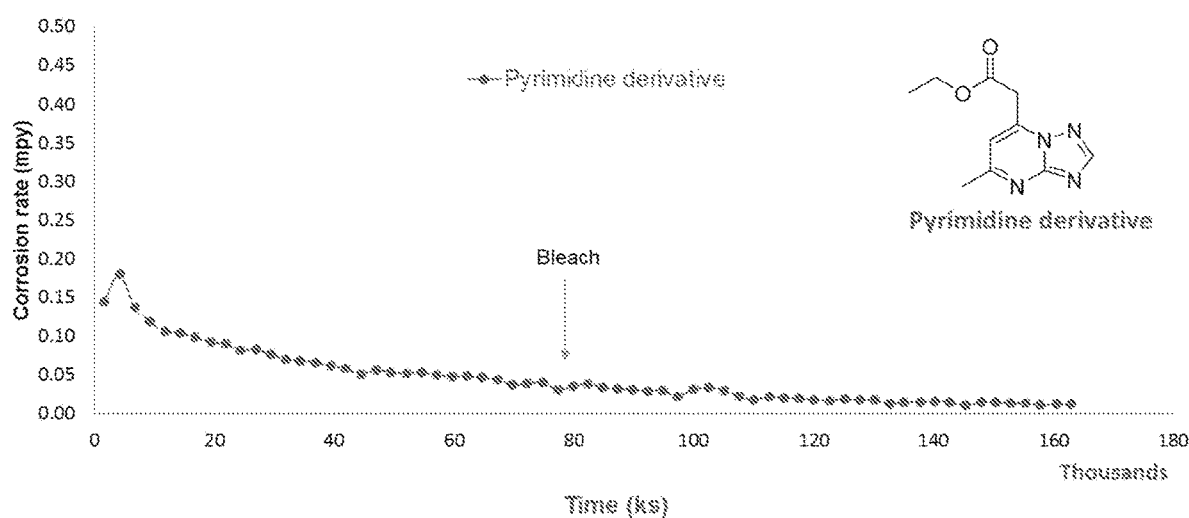

1,2,4-TRIAZOLO[1,5-A] PYRIMIDINE DERIVATIVE AS COPPER CORROSION INHIBITOR

TECHNICAL FIELD

The present disclosure generally relates to corrosion inhibitors and methods of inhibiting corrosion. More specifically, the disclosure relates to 1,2,4-triazolo[1,5,-a] pyrimidine derivatives as corrosion inhibitors and methods of inhibiting corrosion of metallic surfaces in aqueous environments.

BACKGROUND

Copper and copper alloy components are commonly used in industrial systems due to the high thermal conductivity and anti-microbial properties of copper. Copper and copper alloys (e.g., bronze and brass) are relatively resistant to corrosion as a result of protective film layers that naturally coat the surface of copper, which include an inner cuprous oxide film layer and an outer cupric oxide film layer. Under anaerobic conditions, these protective layers generally reduce the rate of further corrosion of the metal surface. However, under certain conditions, copper and copper alloys are susceptible to corrosion. In the presence of oxygen and under acidic conditions oxidation of copper and dissolution of the copper (II) ion into water can occur.

Copper corrosion inhibitors are commonly added to industrial water systems to prevent and reduce dissolution of copper from system surfaces. In particular, the use of nitrogen-containing compounds, such as azoles, is well known for inhibiting the corrosion of copper and copper alloys. It is generally believed that the nitrogen lone pair electrons coordinate to the metal, resulting in the formation of a thin organic film layer that protects the copper surface from elements present in the aqueous system. Nitrogen-containing compounds, such as azoles, are also known to precipitate copper (II) from the aqueous solution, hindering corrosion that can occur due to galvanic reactions between copper and other metals.

Oxidizing halogens are commonly used as biocides in industrial systems to control slime and microbiological growth in water. The protective film provided by many azoles erodes in the presence of oxidizing halogens, such as chlorine, hypochlorite, and hypobromite, thereby reducing the effectiveness of the corrosion inhibitor. Moreover, a decrease in copper (II) precipitation often occurs in the presence of oxidizing halogens due to halogen attack of the corrosion inhibitor in solution. Thus, in the presence of oxidizing halogens, an excess or continuous injection of corrosion inhibitor is often required to maintain the organic protective film.

BRIEF SUMMARY

A method of inhibiting corrosion of a metal surface in contact with an aqueous system is provided. The method may include adding a corrosion inhibitor composition to the aqueous system. The corrosion inhibitor composition may include a compound or salt thereof of formula (I):

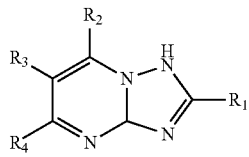

where $R_2$ may be hydrogen, a substituted or unsubstituted $C_1$-$C_4$ alkyl group, —COOR$_5$, —CH$_2$COOR$_5$, chloro, bromo, or iodo; $R_5$ may be hydrogen or a substituted or unsubstituted $C_1$-$C_{20}$ alkyl group; $R_1$, $R_3$, and $R_4$ are each independently hydrogen, a substituted or unsubstituted $C_1$-$C_4$ alkyl group, —COOH, chloro, bromo, or iodo.

In some aspects, $R_4$ may be hydrogen or a substituted or unsubstituted $C_1$-$C_4$ alkyl group.

In some aspects, $R_3$ is hydrogen or a substituted or unsubstituted $C_1$-$C_4$ alkyl group.

In some aspects, the compound or salt thereof of formula (I) is selected from:

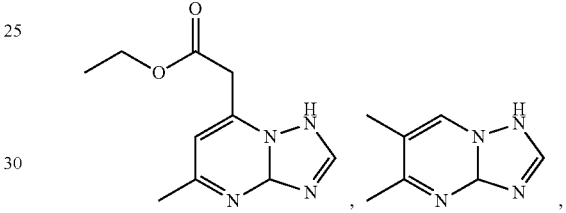

and any combination thereof.

In some aspects, the metal surface comprises iron, copper, an iron alloy, a copper alloy, admiralty brass, about 90% copper and about 10% nickel, about 80% copper and about 20% nickel, about 70% copper and about 30% nickel, aluminium brass, manganese brass, leaded naval bronze, phosphor bronze, or any combination thereof.

In some aspects, the metal surface comprises copper.

In some aspects, the corrosion inhibitor composition may be added to the aqueous system at a dosage rate of from about 0.01 ppm to about 500 ppm.

In some aspects, the aqueous system may include an oxidizing halogen compound.

In some aspects, the oxidizing halogen compound is selected from the group consisting of hypochlorite bleach, chlorine, bromine, hypochlorite, hypobromite, chlorine dioxide, iodine/hypoiodous acid, hypobromous acid, a halogenated hydantoin, and any combination thereof.

In some aspects, the aqueous system may include a non-halogen-containing oxidizing biocide.

In some aspects, the non-halogen-containing oxidizing biocide is selected from the group consisting of: 5-chloro-2-methyl-4-isothiazolin-3-one, 2-methyl-4-isothiazolin-3-one, glutaraldehyde, dibromo propionic acid, quaternary ammonium salts, a peroxide, a persulfate, a permanganate, a peracetic acid, and any combination thereof.

In some aspects, the corrosion inhibitor composition comprises a water-miscible co-solvent.

In some aspects, the water-miscible co-solvent is selected from the group consisting of acetone, methanol, ethanol, propanol, formic acid, formamide, propylene glycol, ethylene glycol, and any combination thereof.

In some aspects, the corrosion inhibitor composition comprises an additive.

In some aspects, the additive is selected from the group consisting of an additional corrosion inhibitor, a treatment polymer, an anti-microbial agent, an anti-scaling agent, a colorant, a filler, a buffer, a surfactant, a viscosity modifier, a chelating agent, a dispersant, a deodorant, a masking agent, an oxygen scavenger, an indicator dye, and any combination thereof.

In some aspects, the aqueous system may be a cooling system, a boiler system, a heating system, a membrane system, a paper making system, a food and beverage system, an oil and gas system, or any system that comprises water.

A corrosion inhibitor composition is provided. The corrosion inhibitor composition may include a compound or salt thereof of formula (I);

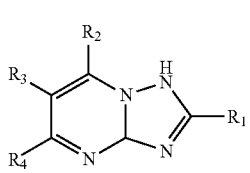

(I)

where $R_2$ may be hydrogen, a substituted or unsubstituted $C_1$-$C_4$ alkyl group, —COOR$_5$, —CH$_2$COOR$_5$, chloro, bromo, or iodo; $R_5$ may be hydrogen or a substituted or unsubstituted $C_1$-$C_{20}$ alkyl group; $R_1$, $R_3$, and $R_4$ are each independently hydrogen, a substituted or unsubstituted $C_1$-$C_4$ alkyl group, —COOH, chloro, bromo, or iodo.

A coating is provided that comprises the corrosion inhibitor composition described herein.

This disclosure also includes a use of the corrosion inhibitor composition described herein for inhibiting corrosion of copper or copper alloys.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which:

FIG. 1 shows a graph depicting corrosion data for pyrimidine derivative before and after addition of bleach to the water.

DETAILED DESCRIPTION

Various embodiments are described below. The relationship and functioning of the various elements of the embodiments may better be understood by reference to the following detailed description. However, embodiments are not limited to those explicitly described herein.

The following definitions are provided to help determine how terms used in this application are to be construed.

"Alkoxy" refers to a moiety of the formula RO—, where R is alkyl, alkenyl, or alkynyl.

"Alkyl" refers to a straight-chain or branched alkyl substituent. Examples of such substituents include, but are not limited to, methyl, ethyl, propyl, isopropyl, n-butyl, sec-butyl, isobutyl, tent-butyl, pentyl, isoamyl, hexyl, and the like.

"Alkylheteroaryl" refers to an alkyl group linked to a heteroaryl group.

"Alkenyl" refers to a straight or branched hydrocarbon having, for example, 2, 3, 4, 5, 6, 7, 8, 9, 10, 11, 12, 13, 14, 15, or 16 carbon atoms, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents.

"Alkylthio" refers to a moiety of the formula RS—, where R is alkyl, aryl, alkenyl, or alkynyl.

"Alkynyl" refers to a straight or branched hydrocarbon having, for example, 2, 3, 4, 5, 6, 7, 8, 9, 10, 11, 12, 13, 14, 15, or 16 carbon atoms, and having one or more carbon-carbon triple bonds. Alkynyl groups include, but are not limited to, ethynyl, propynyl, and butynyl. Alkynyl groups may be unsubstituted or substituted by one or more suitable substituents.

"Aminoalkyl" refers to a nitrogen substituent attached to one or more carbon groups, such as alkyl or aryl.

"Aqueous system" refers to any system containing one or more metallic surfaces/components, which are in contact with water on a periodic or continuous basis.

"Aryl" refers to an unsubstituted or substituted aromatic carbocyclic substituent, as commonly understood in the art, and the term "$C_6$-$C_{10}$ aryl" includes phenyl and naphthyl. It is understood that the term "aryl" applies to cyclic substituents that are planar and comprise 4n+2n electrons, according to Hückel's Rule.

"Carbonyl" refers to a substituent comprising a carbon double bonded to an oxygen. Nonlimiting examples of such substituents include aldehydes, ketones, carboxylic acids, esters, amides, and carbamates.

"Cycloalkyl" refers to a cyclic alkyl substituent containing from, for example, about 3 to about 8 carbon atoms, about 4 to about 7 carbon atoms, or from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups, such as methyl groups, ethyl groups, and the like.

"Halogen" or "halo" refers to F, Cl, Br, and I.

"Halosubstituted alkyl" refers to an alkyl group as described above substituted with one or more halogens, such as chloromethyl, trifluoromethyl, 2,2,2-trichloroethyl, and the like.

"Heteroaryl" refers to a monocyclic or bicyclic 5- or 6-membered ring system, wherein the heteroaryl group is unsaturated and satisfies Hückel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like.

"Industrial water system" means any system that circulates water as a component. Non-limiting examples of "industrial water systems" include cooling systems, boiler systems, heating systems, membrane systems, paper making systems, food and beverage systems, oil and gas systems, and any other system that circulates or includes water.

"Isomer" refers to a molecule that has the same molecular formula as another molecule but has a different chemical structure than the other molecule. An isomer of a molecule has the same number of atoms of each element of the molecule but has a different arrangement of its atoms.

"Mild steel" refers to carbon and low alloy steels.

"Oxidizing halogen" refers to an oxidizing agent comprising at least one halogen. Examples of oxidizing halogens include, but are not limited to, chlorine bleach, chlorine, bromine, iodine, hypochlorite, hypobromite, iodine/hypoiodous acid, hypobromous acid, halogenated hydantoins, chlorine dioxide, stabilized versions of hypochlorous or hypobromous acids, and compounds or chemical groups capable of releasing chlorine, bromine, or iodine.

"Water" means any substance that has water as a component or a primary component. Water may include pure water, tap water, fresh water, recycled water, brine, steam, and/or any aqueous solution or aqueous blend.

The present disclosure relates to corrosion inhibitor compositions, methods of inhibiting corrosion, and formulations useful for inhibiting corrosion. Inhibiting corrosion includes, for example, reducing corrosion, completely eliminating corrosion or prohibiting corrosion from occurring for some period of time, lowering a rate of corrosion, etc. In some aspects, the corrosion inhibitor compositions are useful for inhibiting corrosion of metallic surfaces in aqueous environments. In some aspects, the corrosion inhibitor compositions and/or formulations comprise one or more 1,2,4-triazolo[1,5,-a] pyrimidine derivatives.

For example, in some aspects, a corrosion inhibitor composition or formulation may comprise ethyl 2-(5-methyl-1,3a-dihydro-[1,2,4]triazolo[1,5-a]pyrimidin-7-yl)acetate, and/or any analogue, isomer, and/or derivative thereof. In some aspects, a corrosion inhibitor composition or formulation may comprise 5,6-dimethyl-1,3a-dihydro-[1,2,4]triazolo[1,5-a]pyrimidine, and/or any analogue, isomer, and/or derivative thereof. As will be described and exemplified below, the pyrimidine derivatives disclosed herein display superior performance as corrosion inhibitors and the inhibition efficiency was found to increase with an increase in the concentration of these corrosion inhibitors. The presently disclosed pyrimidine derivatives also have a high tolerance to calcium hardness and bleach. For example, in some aspects, the corrosion inhibitor compositions and formulations disclosed herein achieve a corrosion rate of less than 0.1 mpy in the presence and in the absence of bleach.

The presently disclosed corrosion inhibitor compositions may comprise one of the following compounds or any combination of any of the compounds of formula (I):

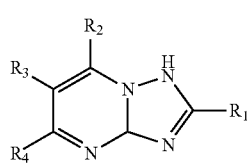

(I)

where $R_2$ may be hydrogen, a substituted or unsubstituted $C_1$-$C_4$ alkyl group, —COOR$_5$, —CH$_2$COOR$_5$, chloro, bromo, or iodo; $R_5$ may be hydrogen or a substituted or unsubstituted $C_1$-$C_{20}$ alkyl group; $R_1$, $R_3$, and $R_4$ are each independently hydrogen, a substituted or unsubstituted $C_1$-$C_4$ alkyl group, —COOH, chloro, bromo, or iodo.

In some aspects, $R_1$ is hydrogen.

In some aspects, $R_2$ is hydrogen or —CH$_2$COOR$_5$.

In some aspects, $R_3$ is hydrogen or a substituted or unsubstituted $C_1$-$C_4$ alkyl group.

In some aspects, $R_4$ may be hydrogen or a substituted or unsubstituted $C_1$-$C_4$ alkyl group.

In some aspects, $R_1$ is hydrogen and $R_4$ is a substituted or unsubstituted $C_1$-$C_4$ alkyl group.

In some aspects, $R_1$ and $R_2$ are hydrogen, $R_3$ and $R_4$ are each independently a substituted or unsubstituted $C_1$-$C_4$ alkyl group.

In some aspects, $R_1$ and $R_3$ are hydrogen, $R_4$ is a substituted or unsubstituted $C_1$-$C_4$ alkyl group, and $R_2$ is —CH$_2$COOR$_5$.

In some aspects, the compound or salt thereof of formula (I) is selected from:

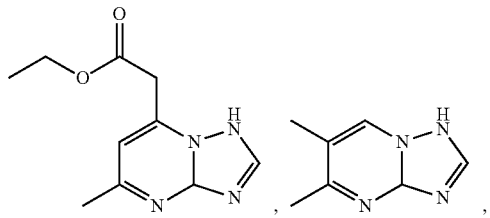

and any combination thereof.

In some aspects, a coating is provided that comprises the corrosion inhibitor composition described herein. The coating may comprise one or more of the compounds of formula (I). In some aspects, the coating may comprise a compound selected from:

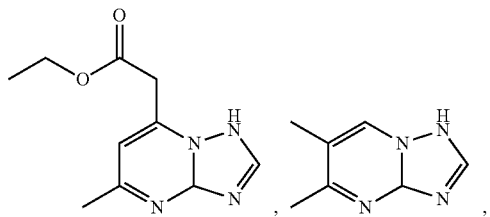

and any combination thereof.

A method of inhibiting corrosion of a metal surface in contact with an aqueous system is provided. The method may include adding a corrosion inhibitor composition to the aqueous system.

The corrosion inhibitor composition may include a compound or salt thereof of formula (I) as described herein.

The corrosion inhibitor compositions/formulations disclosed herein may provide corrosion protection for any metal including, but not limited to, iron, copper, iron alloys, copper alloys, admiralty brass, copper nickel (90/10, 80/20 and 70/30), aluminium brass, manganese brass, leaded naval bronze, and phosphor bronze.

In some aspects, the metal surface comprises iron, copper, an iron alloy, a copper alloy, admiralty brass, about 90% copper and about 10% nickel, about 80% copper and about 20% nickel, about 70% copper and about 30% nickel, aluminium brass, manganese brass, leaded naval bronze, phosphor bronze, or any combination thereof.

The presently disclosed corrosion inhibitor compositions/formulations may also be used to protect silver, steel (e.g., galvanized steel) and/or aluminum, for example.

A corrosion inhibitor composition and/or formulation as disclosed herein can be used to protect any copper alloy, including bronze and brass.

Bronze commonly comprises copper and tin, but may comprise other elements including aluminum, manganese, silicon, arsenic, and phosphorus. Brass comprises copper and zinc is commonly used in piping in water boiler systems. In certain aspects, a corrosion inhibitor composition and/or formulation as disclosed herein is added to an aqueous system in contact with a metal surface comprising bronze to inhibit metal corrosion. In certain aspects, a corrosion inhibitor composition and/or formulation as disclosed herein is added to an aqueous system in contact with a metal surface comprising brass to inhibit metal corrosion. In certain aspects, a corrosion inhibitor composition and/or formulation as disclosed herein is added to an aqueous system in contact with a metal surface comprising a copper-nickel alloy to inhibit metal corrosion.

In certain aspects, a corrosion inhibitor composition and/or formulation as disclosed herein inhibits the corrosion of mild steel. In certain embodiments, a corrosion inhibitor composition and/or formulation as disclosed herein inhibits the corrosion of metal alloys including, but not limited to, galvanized steel, stainless steel, cast iron, nickel, and combinations thereof.

In certain aspects, a corrosion inhibitor composition and/or formulation as disclosed herein inhibits pitting corrosion of a metallic surface, such as a surface comprising mild steel.

The metal corrosion rate provided by a corrosion inhibitor composition and/or formulation as disclosed herein is not limited. In certain embodiments, a corrosion inhibitor composition and/or formulation as disclosed herein provides a metal corrosion rate that is acceptable according to industry standards, e.g., about 0.2 mpy or less. In certain aspects, a corrosion inhibitor composition and/or formulation as disclosed herein provides a metal corrosion rate of about 0.1 mpy or less. In additional aspects, a corrosion inhibitor composition and/or formulation as disclosed herein provides a metal corrosion rate of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

While a corrosion inhibitor composition and/or formulation as disclosed herein can be added to an aqueous system at any dosage rate, it is generally added to an aqueous system at a dosage rate of from about 0.01 ppm to about 500 ppm. In certain aspects, a corrosion inhibitor composition and/or formulation as disclosed herein is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

The corrosion inhibitor compositions and/or formulations as disclosed herein can be used to inhibit corrosion of metal in an aqueous system having any pH. In certain aspects, a corrosion inhibitor composition and/or formulation as disclosed herein is added to an aqueous system having a pH of from about 6 to about 12, from about 6 to about 11, from about 6 to about 10, from about 6 to about 9, from about 6 to about 8, from about 7 to about 12, from about 8 to about 12, from about 9 to about 12, from about 7 to about 10, or from about 8 to about 10.

An advantage of the corrosion inhibitor compositions and/or formulations as disclosed herein is that they generally provide corrosion protection for metal surfaces in the presence of oxidizing halogen compounds. In certain embodiments, a corrosion inhibitor composition and/or formulation as disclosed herein inhibits metal corrosion in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof.

The metal corrosion rate provided by the corrosion inhibitor compositions and/or formulations in the presence of an oxidizing compound is not limited. In certain aspects, a corrosion inhibitor composition and/or formulation as disclosed herein provides a metal corrosion rate in the presence of an oxidizing halogen compound of about 0.2 mpy or less. In certain aspects, a corrosion inhibitor composition and/or formulation as disclosed herein provides a metal corrosion rate in the presence of an oxidizing halogen compound of about 0.1 mpy or less, such as about 0.05 mpy or less, about 0.04 mpy or less, about 0.03 mpy or less, about 0.02 mpy or less, about 0.01 mpy or less, about 0.005 mpy or less, or about 0.002 mpy or less. In certain aspects, the metal corrosion rate provided by a corrosion inhibitor composition and/or formulation as disclosed herein is essentially the same in the absence or presence of an oxidizing halogen compound.

In certain aspects, a corrosion inhibitor composition and/or formulation as disclosed herein inhibits metal corrosion when added to an aqueous system comprising a non-halogen-containing oxidizing biocide including, but not limited to, peroxides (e.g., hydrogen peroxide), persulfates, permanganates, and peracetic acids.

Another advantage of using the corrosion inhibitor compositions and/or formulations as disclosed herein is a smaller amount of oxidizing halogen compound is required to maintain low microbial levels because the corrosion inhibitor compositions and/or formulations as disclosed herein generally have reduced interactions with the oxidizing halogen compound. Furthermore, halogenated azoles that result from the reaction between an azole and oxidizing agent are known to be environmentally undesirable due to their toxicity. Thus, another advantage of the present disclosure is that the corrosion inhibitor compositions and/or formulations as disclosed herein are resistant (or essentially resistant) to halogen attack, and do not lead to the release of halogenated azoles into the environment.

In some aspects, the aqueous system is a cooling water system. The cooling water system can be a closed loop cooling water system or an open loop cooling water system. In some aspects, a corrosion inhibitor composition and/or formulation as disclosed herein is added to a closed loop cooling water system at a dosage rate of from about 0.01 ppm to about 200 ppm. In some aspects, a corrosion inhibitor composition and/or formulation as disclosed herein is added to an open loop cooling water system at a dosage rate of from about 0.01 ppm to about 20 ppm.

The corrosion inhibitor compositions and/or formulations as disclosed herein are contacted with a metal surface by any suitable method. In certain embodiments, a corrosion inhibitor composition (or solution comprising the composition) and/or formulation as disclosed herein is contacted with a metal surface by immersion, spraying, or other coating techniques. In certain embodiments, a corrosion inhibitor composition and/or formulation is introduced into the water of the aqueous system by any conventional method, such as manually or automatically using a chemical injection pump, and is fed into the aqueous system on either a periodic or continuous basis.

In certain aspects, if a corrosion inhibitor composition and/or formulation as disclosed herein is relatively insoluble in water, the composition may be made soluble by forming an organic or inorganic salt of one or more of the compounds within the composition/formulation. Thus, in certain aspects, a corrosion inhibitor composition and/or formulation as disclosed herein comprises a water-soluble salt of one or more of the compounds disclosed herein. In certain aspects, a corrosion inhibitor composition and/or formulation as disclosed herein is added as a solution in a water-miscible co-solvent including, but not limited to, acetone, methanol, ethanol, propanol, formic acid, formamide, propylene glycol, or ethylene glycol. In certain embodiments, a co-solvent is used to achieve maximum solubility of a corrosion inhibitor composition and/or formulation as disclosed herein in the aqueous system. In certain aspects, low molecular weight polyethylene glycol, polypropylene glycol, a surfactant (e.g., organic sulfonic acid), or combinations thereof are used to increase the solubility of a corrosion inhibitor composition and/or formulation as disclosed herein.

Those skilled in the art will appreciate that the corrosion inhibitor compositions and/or formulations disclosed herein can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more corrosion inhibitor compositions as disclosed herein. Moreover, the corrosion inhibitor compositions and/or formulations disclosed herein can be added to an aqueous system in combination with a variety of additional corrosion inhibitors including, but not limited to, azoles, orthophosphate, polyphosphates, phosphonates, molybdates, silicates, oximes, and nitrites.

The corrosion inhibitor compositions and/or formulations disclosed herein also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

Certain embodiments of the formulation also comprise a base, such as sodium hydroxide. In some aspects, sodium hydroxide may be added to the formulation as a 50% aqueous solution. In some aspects, sodium hydroxide is added until the formulation has a pH of about 9 to about 10.

The formulation may comprise various amounts of each component. For example, the formulation may comprise about 70% by weight water and about 30% by weight of one or more corrosion inhibitor compounds. The formulations may also comprise a base, such as sodium hydroxide, in whatever amount is necessary to achieve the desired pH. In some embodiments, the formulation may comprise from about 1% to about 10% base, from about 80% to about 60% water, and from about 40% to about 20% of one or more corrosion inhibitor compounds. In certain embodiments, the formulation comprises about 1% base, about 69% water, and about 30% of one or more corrosion inhibitor compounds.

In some aspects, a formulation is obtained by dissolving a corrosion inhibitor compound, such as bis-benzotriazole, in water. The pH of the water may be from about 9 to about 10. pH adjustment may help make the corrosion inhibitor compound soluble in water. pH adjustment can be accomplished using a base, such as diluted NaOH (about 50% in water). The formulation may comprise one or more corrosion inhibitor compounds.

The corrosion inhibitor compositions and/or formulations as disclosed herein can be added to an aqueous system in any form. In certain aspects, a corrosion inhibitor composition and/or formulation is added to an aqueous system as a dried solid. In certain embodiments, a corrosion inhibitor composition and/or formulation is added to an aqueous system as a solution in a co-solvent miscible with water. In certain embodiments, a corrosion inhibitor composition and/or formulation as disclosed herein is added to an aqueous system as an aqueous solution.

In certain aspects, a corrosion inhibitor composition and/or formulation as disclosed herein is added to a laundry system, a warewashing system, an aqueous system that recirculates water, and/or an aqueous system that has stagnant water.

The corrosion inhibitor compositions, formulations, and methods of inhibiting corrosion disclosed herein can be applied to open loop or closed loop recirculating water systems, such as cooling water systems. Certain aspects of the presently disclosed corrosion inhibitor compositions and/or formulations achieve corrosion rates of 0.2 mpy or less, and these low rates can be achieved in the presence or absence of bleach. In some aspects, the temperature of the water in the aqueous system may be up to about 60° C., such as from about 10° C. to about 60° C. In certain embodiments, the presently disclosed corrosion inhibitor compositions and/or formulations have a chloride tolerance up to about 1000 ppm as Cl. Additionally, in certain aspects, the presently disclosed corrosion inhibitor compositions and/or formulations are stable for a Holding time index of about 150 hours.

EXAMPLES

The following examples further illustrate certain embodiments of the present disclosure but should not be construed in any way as limiting the scope of the present disclosure.

Synthesis Procedure:

A mixture of the 3-amino-1,2,4-triazole (10.0 mmol) and 4-hydroxy-6-methyl-2H-pyran-2-one acetone (12.5 mmol) in 30 ml of ethanol was refluxed for 12 hours (Scheme 1). After cooling, the reaction mixture was allowed to stand overnight and then filtered to give the solid triazolopyrimidine products, which were crystallized from ethanol.

A mixture of the 3-amino-1,2,4-triazole (10.0 mmol) and acetyl acetone (12.5 mmol) in 30 ml of ethanol was refluxed for 12 hours (Scheme 2). After cooling, the reaction mixture was allowed to stand overnight and then filtered to give the solid triazolopyrimidine products, which were crystallized from ethanol.

Scheme 1

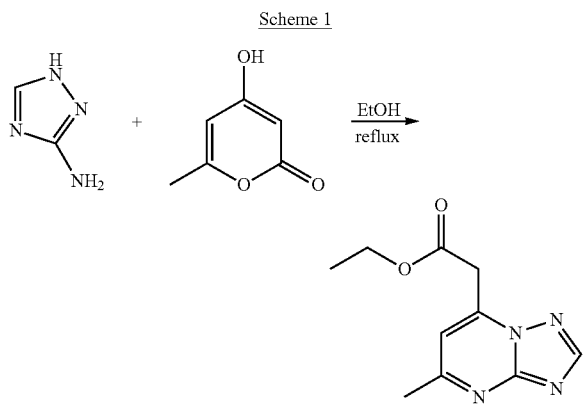

Scheme 2

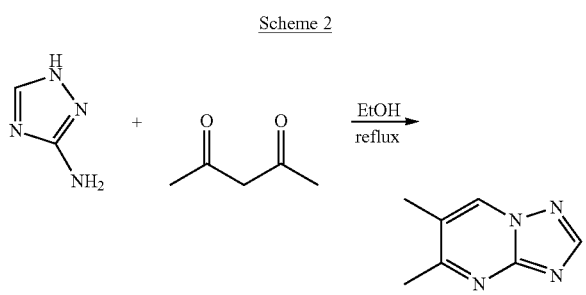

Example 1: Corrosion Performance of Pyrimidine Derivative

Various electrochemical experiments were carried out. The pH of the test water was maintained at about 7 in each experiment using carbon dioxide. The water temperature was maintained at about 45° C. throughout the experiment. Copper coupon samples were immersed in 1 liter electrochemical cells comprising a corrosion inhibitor (about 5 ppm active) and the Rp (polarization resistance) was recorded over a 48-hour period. From about 24 hours to about 48 hours, a few microliters of bleach was added to obtain a FRC (free residual chlorine) level of about 0.5 to about 1.2 ppm. The analysis was conducted using the following testing conditions: initial E: about −0.02V; final E: about +0.02V; scan rate: about 0.5 mV/s; sample period: about 1 second; repeat time: about 15 minutes; sample area: about 5 cm$^2$; density: about 8.89 g/cm$^3$.

The results of the experiment are depicted in FIG. 1. As can be seen, corrosion inhibitor ethyl 2-(5-methyl-1,3a-dihydro-[1,2,4]triazolo[1,5-a]pyrimidin-7-yl)acetate was tested. The x-axis depicts the corrosion rate (mpy). Bleach was added after about 70,000 seconds and the FRC was maintained from about 0.5 to about 1.2 ppm. In comparison to tolyltriazole (TT) and benzotriazole (BZT), the corrosion rate of 1,2,4-triazolo[1,5,-a] pyrimidine derivative was very low in the presence of biocide as well as in the absence of biocide.

Any composition/formulation disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions, formulations, and methods disclosed and claimed herein can be made and executed without undue experimentation in light of the present disclosure. While this invention may be embodied in many different forms, there are described in detail herein specific embodiments of the invention. The present disclosure is an exemplification of the principles of the invention and is not intended to limit the invention to the particular embodiments illustrated.

In addition, unless expressly stated to the contrary, use of the term "a" is intended to include "at least one" or "one or more." For example, "a corrosion inhibitor compound" is intended to include "at least one corrosion inhibitor compound" or "one or more corrosion inhibitor compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:
1. A method of inhibiting corrosion of a metal surface in contact with an aqueous system, comprising:
  adding a corrosion inhibitor composition to the aqueous system, the corrosion inhibitor composition comprising a compound or salt thereof of formula (I);

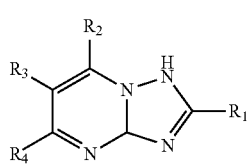

(I)

wherein:
R$_2$ is hydrogen, a substituted or unsubstituted C$_1$-C$_4$ alkyl group, —COOR$_5$, —CH$_2$COOR$_5$, chloro, bromo, or iodo;
R$_5$ is hydrogen or a substituted or unsubstituted C$_1$-C$_{20}$ alkyl group; and
R$_1$, R$_3$, and R$_4$ are each independently hydrogen, a substituted or unsubstituted C$_1$-C$_4$ alkyl group, —COOH, chloro, bromo, or iodo; and
wherein:
the aqueous system comprises an oxidizing halogen compound; and
the aqueous system has a pH of from about 6 to about 12, provided that at least one of R$_2$, R$_3$, and R$_4$ is not hydrogen.

2. The method of claim 1, wherein the metal surface comprises iron, copper, an iron alloy, a copper alloy, admiralty brass, about 90% copper and about 10% nickel, about 80% copper and about 20% nickel, about 70% copper and about 30% nickel, aluminium brass, manganese brass, leaded naval bronze, phosphor bronze, or any combination thereof.

3. The method of claim 1, wherein the metal surface comprises copper.

4. The method of claim 1, wherein R$_4$ is hydrogen or a substituted or unsubstituted C$_1$-C$_4$ alkyl group.

5. The method of claim 1, wherein R$_4$ is a substituted or unsubstituted C$_1$-C$_4$ alkyl group, —COOH, chloro, bromo, or iodo.

6. The method of claim 1, wherein R$_3$ is hydrogen or a substituted or unsubstituted C$_1$-C$_4$ alkyl group.

7. The method of claim 1, wherein the compound or salt thereof of formula (I) is selected from:

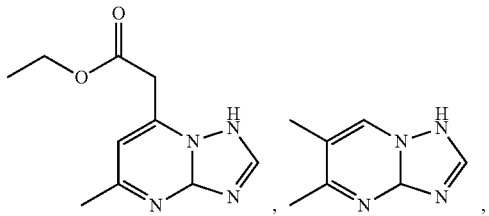

and any combination thereof.

8. The method of claim 1, wherein the corrosion inhibitor composition is added to the aqueous system at a dosage rate of from about 0.01 ppm to about 500 ppm.

9. The method of claim 1, wherein the oxidizing halogen compound is selected from the group consisting of hypochlorite bleach, chlorine, bromine, hypochlorite, hypobromite, chlorine dioxide, iodine/hypoiodous acid, hypobromous acid, a halogenated hydantoin, 5-chloro-2-methyl-4-isothiazolin-3-one, dibromo propionic acid, and any combination thereof.

10. The method of claim 1, wherein the aqueous system further comprises a non-halogen-containing oxidizing biocide.

11. The method of claim 10, wherein the non-halogen-containing oxidizing biocide is selected from the group consisting of: 2-methyl-4-isothiazolin-3-one, glutaraldehyde, quaternary ammonium salts, a peroxide, a persulfate, a permanganate, a peracetic acid, and any combination thereof.

12. The method of claim 1, wherein the corrosion inhibitor composition further comprises a water-miscible solvent.

13. The method of claim 12, wherein the water-miscible solvent is selected from the group consisting of acetone, methanol, ethanol, propanol, formic acid, formamide, propylene glycol, ethylene glycol, and any combination thereof.

14. The method of claim 1, wherein the corrosion inhibitor composition further comprises an additive.

15. The method of claim 14, wherein the additive is selected from the group consisting of an additional corrosion inhibitor, a treatment polymer, an anti-microbial agent, an anti-scaling agent, a colorant, a filler, a buffer, a surfactant, a viscosity modifier, a chelating agent, a dispersant, a deodorant, a masking agent, an oxygen scavenger, an indicator dye, and any combination thereof.

16. The method of claim 1, wherein the aqueous system is a cooling system, a boiler system, a heating system, a membrane system, a paper making system, a food and beverage system, or an oil and gas system.

17. The method of claim 1, wherein the corrosion inhibitor composition further comprises a base.

18. A method of inhibiting corrosion of a metal surface in contact with an aqueous system, comprising:
adding a corrosion inhibitor composition to the aqueous system, the corrosion inhibitor composition comprising one or more compounds, or salts thereof, of formula (I);

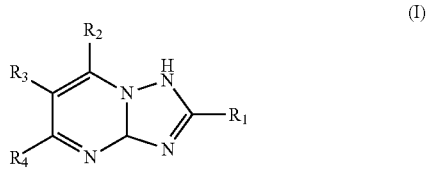

wherein:
R$_2$ is hydrogen, a substituted or unsubstituted C$_1$-C$_4$ alkyl group, —COOR$_5$, —CH$_2$COOR$_5$, chloro, bromo, or iodo;
R$_5$ is hydrogen or a substituted or unsubstituted C$_1$-C$_{20}$ alkyl group; and
R$_1$, R$_3$, and R$_4$ are each independently hydrogen, a substituted or unsubstituted C$_1$-C$_4$ alkyl group, —COOH, chloro, bromo, or iodo; and
wherein the aqueous system comprises an oxidizing halogen compound, provided that:
at least one of R$_2$, R$_3$, and R$_4$ is not hydrogen;
the corrosion inhibitor composition excludes additional corrosion inhibitors; and
the method excludes adding additional corrosion inhibitors.

* * * * *